(12) United States Patent
Staib et al.

(10) Patent No.: US 8,527,024 B2
(45) Date of Patent: Sep. 3, 2013

(54) AMPEROMETRIC SENSOR AND METHOD FOR ITS MANUFACTURING

(75) Inventors: Arnulf Staib, Heppenheim (DE); Reinhold Mischler, Ludwigshafen (DE); Martin Hajnsek, Graz (AT); Harvey Buck, Indianapolis, IN (US); Walter Jernigan, Carmel, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 849 days.

(21) Appl. No.: 12/339,945

(22) Filed: Dec. 19, 2008

(65) Prior Publication Data

US 2009/0099433 A1 Apr. 16, 2009

Related U.S. Application Data

(63) Continuation of application No. PCT/EP2007/004606, filed on May 24, 2007.

(60) Provisional application No. 60/805,151, filed on Jun. 19, 2006.

(51) Int. Cl.
*G01N 33/487* (2006.01)
*G01N 27/49* (2006.01)
*G01N 27/26* (2006.01)

(52) U.S. Cl.
USPC ............... 600/345; 204/403.1; 204/403.11; 204/403.13

(58) Field of Classification Search
None
See application file for complete search history.

(56) References Cited

U.S. PATENT DOCUMENTS

| 885,476 A | 4/1908 | Hogrebe et al. |
| 4,392,933 A | 7/1983 | Nakamura et al. |
| 5,160,418 A | 11/1992 | Mullen |
| 5,593,852 A * | 1/1997 | Heller et al. ............... 435/14 |

(Continued)

FOREIGN PATENT DOCUMENTS

| EP | 0247850 B1 | 4/1993 |
| EP | 0603154 B1 | 8/1998 |

(Continued)

OTHER PUBLICATIONS

Dai et al., "Glucose Biosensor Based on Multi-Walled Carbon Nanotube Modified Glassy Carbon Electrode," Electroanalysis, 2004, vol. 16, issue 20, pp. 1697-1703.*

(Continued)

*Primary Examiner* — Shafiqul Haq
*Assistant Examiner* — Galina Yakovleva
(74) *Attorney, Agent, or Firm* — Bose McKinney & Evans LLP

(57) ABSTRACT

An in vivo amperometric sensor is provided for measuring the concentration of an analyte in a body fluid. The sensor comprises a counter electrode and a working electrode, and the working electrode comprises a sensing layer which is generally water permeable and arranged on a support member adjacent to a contact pad. The sensing layer comprises an immobilized enzyme capable of acting catalytically in the presence of the analyte to cause an electrical signal. The sensing layer has an upper surface facing the body fluid and a lower surface facing away from the body fluid, and the immobilized enzyme is distributed within the sensing layer in such a way that the enzyme concentration in the middle between the upper and lower surfaces is at least as high as on the upper surface of the sensing layer.

29 Claims, 3 Drawing Sheets

(56) References Cited

U.S. PATENT DOCUMENTS

| | | | |
|---|---|---|---|
| 5,616,222 | A | 4/1997 | Maley et al. |
| 5,882,494 | A | 3/1999 | Van Antwerp |
| 6,175,752 | B1 | 1/2001 | Say et al. |
| 6,300,306 | B1 | 10/2001 | Firkins et al. |
| 6,509,148 | B2 | 1/2003 | Cha et al. |
| 6,721,587 | B2 | 4/2004 | Gough |
| 7,045,054 | B1 | 5/2006 | Buck et al. |
| 2004/0111017 | A1 | 6/2004 | Say et al. |
| 2004/0137547 | A1 | 7/2004 | Shah et al. |
| 2004/0219664 | A1 | 11/2004 | Heller et al. |
| 2005/0090607 | A1 | 4/2005 | Tapsak et al. |
| 2005/0103625 | A1 | 5/2005 | Rhodes et al. |
| 2005/0244811 | A1 | 11/2005 | Soundarrajan et al. |
| 2006/0015020 | A1 | 1/2006 | Neale et al. |
| 2007/0135698 | A1 | 6/2007 | Shah et al. |

FOREIGN PATENT DOCUMENTS

| | | |
|---|---|---|
| EP | 0709679 B1 | 7/1999 |
| EP | 1661516 A1 | 5/2006 |
| EP | 1630234 B1 | 12/2008 |
| WO | 0121827 A1 | 3/2001 |
| WO | 2004007756 A1 | 1/2004 |
| WO | 2005032362 A2 | 4/2005 |
| WO | 2005088288 A1 | 9/2005 |
| WO | 2007070486 A2 | 6/2007 |

OTHER PUBLICATIONS

Tran-Minh et al., "Construction and study of electrodes using cross-linked enzymes," Anal. Chem., 1975, 47 (8), pp. 1359-1364.*

James F. Castner et al., Mass Transport Reaction Kinetic Parameters Determined Electrochemically for Immobilized Glucose Oxidase, Biochemistry, 1984, 23, p. 2203-2210.

Jason J. Davis et al., The immobilisation of proteins in carbon nanotubes, Inorganica Chimica Acta 272, 1998, p. 261-266.

Ben Feldman et al., A Continuos Glucose Sensor Based on Wired Enzyme Technology, Diabetes Technology & Therapeutics, vol. 5, No. 5, 2003; p. 769-779.

Dohoon Lee et al., Simple Fabrication of a Highly Sensitive and Fast Glucose Biosensor Using Enzymes Immobilized in Mesocellular Carbon Foam, Advanced Materials, 2005, 17, p. 2828-2833.

John K. Leypoldt et al., Model of a Two-Substrate Enzyme Electrode for Glucose, Anal. Chem., 1984, 56, p. 2896-2904.

San Hua Lim et al., A glucose biosensor based on electrodeposition of palladium nanoparticles and glucose oxidaseonto Nafion-solubilized carbon nanotube electrode, Biosensors and Bioelectronics 20, 2005, p. 2341-2346.

Xi-Liang Luo et al., A novel glucose ENFET based on the special reactivity of $MnO_2$ nanoparticles, Biosensors and Bioelectronics 19, 2004, p. 1295-1300.

McMahon et al., Design variations of a polymer-enzyme composite biosensor for glucose: Enhanced analyte sensitivity without increased oxygen dependence, Journal of Electroanalytical Chemistry 580, 2005, p. 193-202.

A. Mang et al., Biocompatibiltiy of an Electrochemical Sensor for Continuous Glucose Monitoring in Subcutaneous Tissue, Diabetes Technology & Therapeutics, vol. 7, No. 1, 2005, p. 163-173.

Tanja Nowak et al., Biocompatibility of MPC: in vivo evaluation for clinical application, The Japanese Society for Artificial Organs, 2000, 3:39-46.

J. Wang et al., Improved Performance of Carbon Paste Amperometric Biosensors through the Incorporation of Fumed Silica, Electroanalysis, vol. 6, 1994, p. 571-575.

Joseph Wang et al., Oxygen-Rich Oxidase Enzyme Electrodes for Operation in Oxygen-Free Solutions, J. Am. Chem. Soc., 1998,120, p. 1048-1050.

W. Kenneth Ward et al., A Fully Implantable Subcutaneous Glucose Sensor Array: Enhanced Accuracy from Multiple Sensing Units and a Median-Based Algorithm, Diabetes Technology & Therapeutics, vol. 5, No. 6, 2003, p. 943-952.

Jing-Juan Xu et al., Application of $MnO_2$ nanoparticles as an eliminator of ascorbate interference to amperometric glucose biosensors, Electrochemistry Communications, 6, 2004, p. 1169-1173.

Jin-Juan Xu et al., A sensitive biosensor for lactate based on layer-by-layer assembling $MnO_2$ nanoparticles and lactate oxidase on ion-sensitive filed-effect transistors, Chemical Communications, DOI: 10.1039/b416548a, 2004, p. 1-8.

PCT International Search Report and Written Opinion mailed Aug. 22, 2007.

Zhang, J.; Zhang, S-Y.; Xu, J-J.; Chen, H-Y.; "Amorphous Selenium Nanoparticles: Synthesis in Horseradish Peroxidase Cross-linked and Application in Biosensor," Chinese Journal of Inorganic Chemistry, (2006) vol. 22, No. 3, 431-434.

* cited by examiner

AMPEROMETRIC SENSOR AND METHOD FOR ITS MANUFACTURING

CLAIM OF PRIORITY

The present application is continuation of PCT/EP 2007/004606, filed May 24, 2007, which claims priority to U.S. Provisional Application No. 60/805,151, filed Jun. 19, 2006, each of which are hereby incorporated by reference in their entireties.

TECHNICAL FIELD OF THE INVENTION

The present application relates to implantable sensors, particularly to such sensors for in vivo amperometric determination of analyte concentration, and more particularly to an amperometric sensor configured for implantation into the living body of a human or animal to measure the concentration of an analyte in a body fluid, comprising a counter electrode and a working electrode that comprises a generally water permeable sensing layer comprising an immobilized enzyme capable of acting catalytically in the presence of the analyte to cause an electrical signal.

BACKGROUND

Sensors of the general type discussed in the context of the present invention are generally known; see, e.g., EP 0 247 850. Implantable sensors for the in vivo-measurement of medically important analytes like glucose or lactate are based on electrochemical enzymatic detection of the analyte. The most common approach is the use of an oxidase to oxidize an analyte, e.g. glucose, with subsequent reduction of oxygen to hydrogen peroxide and amperometric detection of the hydrogen peroxide by a working electrode of the sensor. Another approach in the field of in-vivo sensing bypasses the use of oxygen/peroxide as a mediator couple by employing synthetic redox mediators for glucose conversion without oxygen. In that case, synthetic redox mediators are built into the sensing element. An example for this approach utilizes poly(biimidizyl)osmium complexes as redox mediators in conjunction with enzyme, as described by Feldmann et al. in Diabetes Technology and Therapeutics, 5, 769 (2003).

Despite intensive research and development efforts there are at present no implantable sensors available which measure medically important analytes like glucose reliably over extended periods of time.

It is an object of the present invention to provide a way to improve the reliability and longevity of amperometric sensors for in vivo-measurements of an analyte concentration in a body fluid.

SUMMARY

According to the invention this object is achieved by an anperometric sensor configured for implantation into the living body of a human or animal to measure the concentration of an analyte in a body fluid, said sensor comprising a counter electrode and a working electrode, said working electrode comprising a sensing layer which is generally permeable for water and arranged on a support member adjacent to a contact pad, said sensing layer comprising an immobilized enzyme capable of acting catalytically in the presence of the analyte to cause an electrical signal, the sensing layer having an upper surface facing the body fluid and a lower surface facing away from the body fluid, wherein the immobilized enzyme is distributed in the sensing layer in such a way that the enzyme concentration in the middle between the upper and lower surfaces is at least as high as on the upper surface of the sensing layer.

In a planar configuration, the contact pad can be placed directly under the sensing layer (or the sensing layer is arranged on the contact pad) both having consistent surface areas. In another embodiment, the contact pad can be made smaller or larger than the sensing layer. In still another embodiment, the contact pad can be partly displaced from the area covered by the sensing layer, so that only a fraction of the sensing layer is in direct contact with the pad. For other arrangements, the contact pad can be placed on one of the sides of the sensing layer. All these options are summarized by the phrase "the sensing layer adjacent to the contact pad". It is understood that this holds likewise for the other electrodes.

It has been found that measurements of implanted amperometric sensors are often adversely affected by a low oxygen concentration in subcutaneous tissue surrounding the sensor. This problem seems to be especially pronounced in the case of enzymatic sensors which rely on an oxidase (for example a glucose oxidase) as the immobilized enzyme in the sensing layer, because such sensors cause an electrical measurement signal by oxidizing the analyte. In principle, the strength of the measurement signal created by such sensors depends on the amount of enzyme, analyte and oxygen present. If the oxygen concentration is sufficiently high, the response of a given sensor with a defined enzyme loading reflects the concentration of the analyte in the vicinity of the sensor and is, in ideal cases, proportional to it. However, if the oxygen concentration is too low, fewer analyte molecules are oxidized and consequently a weaker electrical signal is produced compared to a sensor operating under oxygen-saturated conditions.

Lowering the enzyme loading of a sensor lowers the critical oxygen concentration at which saturation is achieved, but also reduces the signal to noise ratio because a smaller measurement signal is created. Hence, lowering the enzyme loading is not sufficient to solve the problem.

An amperometric sensor according to the present invention deals with the problem of low oxygen concentrations in subcutaneous tissue by means of the sensing layer which comprises the immobilized enzyme which is distributed in the sensing layer in such a way that the enzyme concentration in the middle between the upper and lower surface is at least as high as on the upper surface of the sensing layer.

Accordingly, only a relatively small fraction of the enzyme molecules contained in the sensing layer is active on the upper surface of the sensing layer. As a consequence, a relatively low concentration of oxygen is sufficient to saturate the surface of the sensing layer with oxygen. The structure of the sensing layer allows analyte molecules to diffuse into the sensing layer and interact with enzyme molecules further away from the surface which are surrounded by their own reservoir of oxygen molecules. Thus, the electrical signal of a sensor according to the present invention is created not only within a small surface layer but rather within an extended volume which lowers the oxygen density (oxygen concentration) at which saturation of the sensor is achieved. Consequently, saturation of enzyme with oxygen can be achieved at lower oxygen concentrations without lowering the signal to noise ratio of the measurement signal of the sensor.

Amperometric sensors with a porous sensing layer are known in the art. However, the enzyme is supplied to such sensors only after the porous layer has already been prepared. Therefore, the enzyme concentration of such sensors is typically highest on the upper surface of the sensing layer and decreases strongly with increasing distance from the surface. As a consequence, the major part of the electrical signal of such a sensor is created on the surface of the sensing layer, i.e. in a relatively small volume so that correspondingly higher oxygen concentrations are required for precise measurements.

A distribution of enzyme throughout the sensing layer according to the present invention, especially a homogenous concentration, can be most easily achieved by mixing enzyme into a paste, for example a paste comprising carbon particles and a binder, and applying this mixture onto a contact pad to provide the sensing layer of a working electrode. In one embodiment, a surface-active agent such as a detergent or a hydrophilic polymer is used to aid the dispersion of the enzyme within the paste. In this way an equal distribution of enzyme molecules throughout the sensing layer can be achieved. The object of the invention is therefore also achieved by a method for manufacturing an amperometric sensor configured for implantation into the living body of a human or animal to measure the concentration of an analyte in a body fluid, said method comprising the following steps: mixing carbon particles, enzyme and a polymeric binder to create a paste; applying that paste adjacent to a contact pad onto a support member; and hardening that paste into a porous sensing layer.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
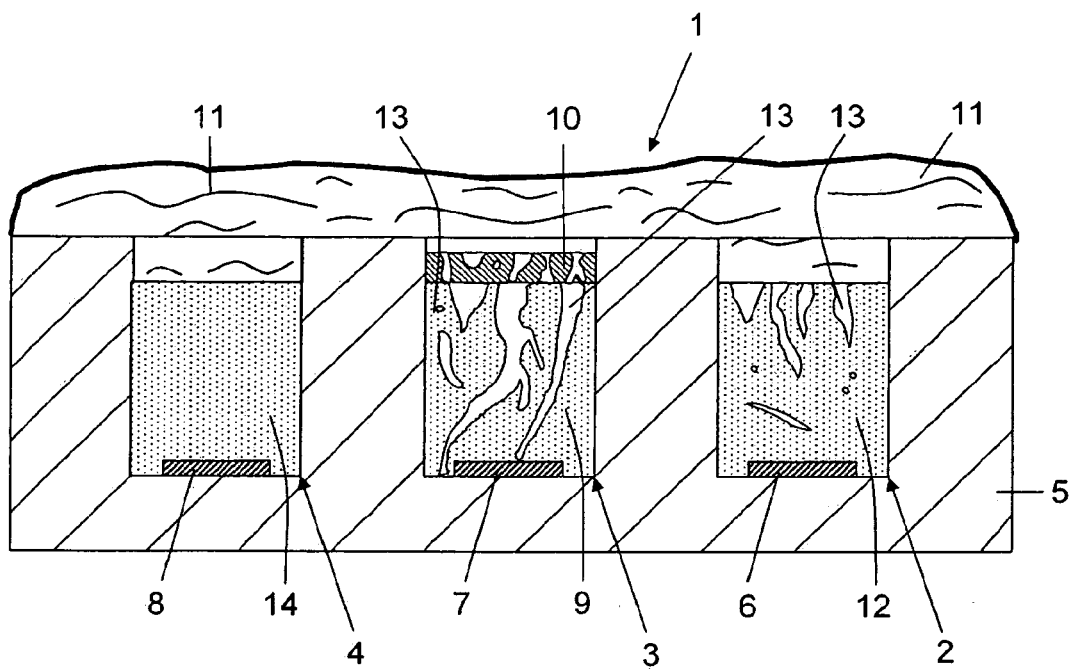
FIG. 1 shows a first exemplary embodiment of a sensor according to the present invention in a cross section view.

FIG. 1 shows schematically a first embodiment of an amperometric sensor 1 configured for implantation into the living body of a human or animal to measure the concentration of an analyte in a body fluid of a human or animal. For better illustration of some details FIG. 1 is not to scale.

In the illustrated embodiment, the sensor 1 comprises a counter electrode 2, a working electrode 3 and a reference electrode 4 which are arranged on a support member 5 which is typically made of a plastic material, such as polyimide. Each electrode 2, 3, 4 comprises a contact pad 6, 7, 8 which is provided as an electrically conductive film, e.g. a metallic film which can be a gold film, with a thickness of between about 50 nm and about 150 nm. It is also possible to make the contact pads 6, 7, 8 from other metals, in particular palladium, or as a multilayer film of different metals. For example, a thin film, less than 20 nm, of titanium covering the support member 5 can be covered with a second film of gold with a thickness of between about 50 nm and about 130 nm, thus forming the contact pads 6, 7, 8. As an alternative, the contact pads 6, 7, 8 can be formed as an electrically conductive polymer film, e.g. from a conductive polymer paste, for example by screen-printing or by dispensing which leads to thicker contact pads 6, 7, 8. Instead of separate counter and reference electrodes 3, 4 a combined counter/reference electrode may also be used. One example of a suitable counter/reference electrode is a silver/silver-chloride electrode. As such counter and/or reference electrodes are commonly used no further description is necessary.

The working electrode 3 further comprises a sensing layer 9 which is generally permeable for water and arranged adjacent to the contact pad 7 of the working electrode 3. The sensing layer 9 comprises immobilized enzyme capable of acting catalytically in the presence of the analyte to cause an electrical signal. In the present example an oxidase, particularly a glucose oxidase is used as enzyme to measure glucose as an analyte in a human body fluid, like interstitial fluid or blood.

The sensing layer 9 was applied as a paste onto the support member 5 to cover the contact pad 7 of the working electrode 2. That paste was made by mixing carbon particles, enzyme and a polymeric binder. In this way the immobilized enzyme is distributed equally throughout the sensing layer 9. A homogeneous enzyme distribution throughout the sensing layer 9 is advantageous. Hence, the enzyme concentration should differ by less than 20%, especially less than 10%, between the upper surface and the lower surface of the sensing layer 9. As the analyte can diffuse into the porous sensing layer 9 the electrical measurement signal is created not just in the sensing layers 9 upper surface which faces away from the contact pad 7 but rather in an extended volume. Therefore, rather low oxygen concentrations are sufficient to saturate the sensor 1 with oxygen and enable precise measurements.

In one embodiment the sensing layer 9 is flat. In other embodiments, the sensing layer 9 is electrically conductive. In yet other embodiments, the electrical conductivity of the sensing layer 9 is at least about 1 $\Omega^{-1}cm^{-1}$. As a result of such conductivity, every place in the sensing layer 9 at which the enzymatic reaction of the analyte takes places acts as a tiny electrode, at which the product of the enzymatic reaction can be quickly reduced or oxidized. In this manner these places are used as cathode or anode, depending on the sign of the electrical potential applied. Consequently the sensing layer 9 in the porous structure comprises a huge number of tiny cathodes or anodes. As a result of this there is no need for the product of the enzymatic reaction to advance through the bulk of the sensing layer 9 which would result in a loss a signal height. An electrically conductive embodiment of the sensing layer 9 therefore has the result of an increased signal height.

The sensing layer 9 of the example shown has a thickness of about 30 μm. Generally the sensing layer 9 should have a thickness of at least about 5 μm, at least 10 μm in one embodiment, in order to provide a sufficiently large volume for the creation of the electrical measurement signal. A thickness of the sensing layer 9 of more than about 100 μm does not provide additional benefits. In other embodiments, the sensing layer 9 has a thickness of between about 20 μm and about 70 μm. In yet other embodiments, the sensing layer 9 is arranged in a depression provided in the support member 5. In this way it is somewhat protected by lateral walls of the depression in the support member 5 from damages during the implantation process. Furthermore, the lateral surfaces of the sensing layer 9 can be connected to the support member 5 and thereby ensure that analyte molecules can diffuse only through the sensing layer's 9 upper surface into the sensing layer 9. Of course, the lateral surfaces can be made generally impervious to water by different means as well. The sensing layer 9 in other embodiments can have lateral surfaces which are generally impervious for the body fluid.

In similar fashion, in one embodiment the contact pads 6, 8 of the counter electrode 2 and the reference electrode 4 are covered with water-permeable layers 12, 14 which were also applied as paste. Of course, the layers 12, 14 of the counter electrode 2 and of the reference electrode 4 contain no enzyme. Like the sensing layer 9, layers 12 and 14 may also comprise carbon particles and a polymeric binder. Whereas porosity enhancing particles 13 like carbon nanotubes have been added to the pastes for the sensing layer 9 and the layer 12, such porosity enhancing particles 13 provide no benefit for the highly conductive layer 14 of the reference electrode 4 and were therefore not added as a matter of design choice. However, such carbon nanotubes may be useful for other purposes, as will be described below, and thus the inclusion of them will not detract from the scope of the present invention.

As enzyme is distributed throughout the whole sensing layer 9, oxygen saturation can be maintained even if much higher analyte concentrations are present at the upper surface of the sensing layer 9 than is feasible for known sensors. The sensing layer of sensors according to prior art is usually covered by a diffusion barrier which hinders analyte diffusion to such an extent that the analyte concentration at the upper surface is typically about 100 times lower than in body fluid surrounding the sensor.

The sensing layer 9 of the sensor 1 of one embodiment of the present invention is covered by a diffusion barrier which hinders diffusion of analyte molecules only to such an extent that, after implantation into the living body of a human or animal, the analyte concentration at the upper surface of the sensing layer 9 is at most about ten times lower than in the body fluid surrounding the implanted sensor 1. In other embodiments it can be at most about five times lower, and in yet other embodiments it can be at most about three times lower. In the example shown, the diffusion barrier comprises several distinct layers 10, 11 contributing to the diffusion resistance of the diffusion barrier against diffusion of analyte molecules.

The diffusion barrier is permeable for the analyte and prevents enzyme from leaking out of the sensing layer 9. In the example shown, the diffusion barrier comprises as a first layer an electrically conductive enzyme-free layer 10 which comprises carbon particles and a polymeric binder and has a thickness of less than a third of the thickness of the sensing layer 9. Usually it is about 1 μm to about 3 μm thick. Like the sensing layer 9 the enzyme-free layer 10 was applied as a paste. That paste differs from the paste of the sensing layer 9 only in that no enzyme was added to it.

The diffusion barrier also comprises a layer 11 which prevents large molecules from clogging pores of the sensing layer 9. The layer 11 may be a dialysis layer which can be provided as a membrane made of cellulose and/or a polymer material. Such a dialysis layer is also an enzyme-free layer and may be applied directly on top of the sensing layer 9 or, as shown in FIG. 1, on top of the electrically conductive enzyme-free layer 10. In one embodiment, such a dialysis layer should hinder analyte diffusion as little as possible. In other embodiments, the layer 11 has an effective diffusion coefficient $D_{eff}$ for the analyte which is at most about ten times lower than the diffusion coefficient D of the analyte in water, and in yet other embodiments it is at most about five times lower than the diffusion coefficient D of the analyte in water. A dialysis layer can be applied as a solid film or applied as a polymer solution which hardens into a dialysis membrane in-situ.

Dialysis membranes are often characterized by their molecular weight cut off (MWCO) which depends on the pore size. The MWCO describes the molecular weight at which a compound will be 90% retained following a night (17-hour) dialysis. The dialysis layer of the example shown has a MWCO of less than about 10 kDalton, and may be less than about 7 kD, and even less than about 5 kD in some embodiments. It has to be understood that MWCOs stated for dialysis layers apply strictly only to globular molecules such as most proteins. More linear molecules may be able to pass through the pores of a dialysis layer, even if their molecular weight exceeds the stated MWCO.

Instead of or in addition to a dialysis membrane, the diffusion barrier may also comprise a polymer layer made of a polymer having a zwitterionic structure to protect the sensing layer 9 and any porous layer 10 from ingression of proteins. A zwitterionic structure enables the rapid uptake of polar protic solvents, in particular water, and such analytes as glucose dissolved within. Hence, polymers having a zwitterionic structure attached to a polymeric backbone are impermeable for proteins but hinder diffusion of analytes like glucose very little. A well-known example for such a polymer is poly(2-methacryloyloxyethyl phosphorylcholine-co-n-butyl-methacrylat) (MPC for short). The MPC polymer layer 11 is applied as a polymer solution comprising ethanol or distilled water and at least 5 wt. % MPC, especially at least 10 wt. % MPC.

In these exemplary embodiments, the diffusion barrier and especially the polymer layer 11, which it comprises, protect the sensor 1 from mechanical damage during the implantation process, prevent enzyme from leaking out of the sensing layer 9 into surrounding tissue, where it might be harmful, and prevents large molecules from clogging pores of the sensing layer 9. It is possible to mix a polymer having a zwitterionic structure like MPC with another polymer, for example polyurethane or typical constituents of the above-mentioned dialyse membranes, in order to tune physical properties of the polymer layer 11.

It is also possible to tune physical properties, such as the permeability for analytes, of the layer 11, if this contains a co-polymer having constituents of different hydrophilicity, by varying the relative amount of each constituent in the co-polymer. In the case of MPC it is possible to increase the relative amount of 2-methacryloyloxyethyl phosphorylcholine versus that of butylmethacrylat from 30:70% to 50:50% yielding a co-polymer with higher permeability towards polar protic solvents or glucose. Another way to increase permeability for polar protic solvent or glucose is to change the hydrophobic backbone of the co-polymer into a more hydrophilic entity. This also applies for other water-soluble analytes.

The sensing layer 9 of the example shown in FIG. 1 contains porous particles 13 to increase its porosity and thereby ease diffusion of analyte molecules into the sensing layer 9. Porous particles 13 in this respect are particles which have voids to adsorb water molecules. These porous particles 13 are added to the paste from which the sensing layer 9 is formed and cause voids through which analyte molecules and water may pass. The porous particles 13 are bound with other particles of the paste by the polymeric binder. Carbon nanotubes are an especially useful additive to increase the porosity of the sensing layer as they tend to form clews, which are only partially filled with carbon particles and binder, and also increase the electrical conductivity of the sensing layer. Silica particles may also be used as porous particles 13 to increase the porosity of the sensing layer 9.

If silica or similar porous particles 13 are used, it is advantageous to use material with a particle size distribution such that the maximum particle size is less than the thickness of the sensing layer 9. In one embodiment, the porous particles 13 should measure at least about 1 µm, and in other embodiments should measure at least about 5 µm. Considering a sensing layer 9 thickness around about 20 µm to about 50 µm, silica FK 320 from Degussa provides adequate particle size, up to about 15 µm. Typically, less than about 10% of this material are mixed into the paste, and can be as low as about 5% or less.

In one embodiment, electrical conductivity is provided throughout the sensing layer 9, so that at each spot of the porous matrix, where a product molecule is generated from the enzymatic reaction, this molecule is directly oxidized or reduced by application of the appropriate voltage without the need for extended diffusion of this molecule to a distant site. Under these circumstances the porous and permeable sensing layer 9 is capable of electrolyzing the analyte substantially throughout the entire layer.

Whatever means for increasing the porosity is used, the mixing of the enzyme with the paste will lead to a fraction of enzyme molecules being accessible to the analyte, either on the upper surface of the sensing layer 9, or at the channels in the vicinity of the additive particles within the sensing layer 9. In one embodiment, the enzyme is immobilized by adsorption and entrapment in the working electrode 3. Entrapment depends not only on the sensing layer 9 but also on properties of the diffusion barrier, i.e. the layer 11, and of the optional enzyme-free layer 10. It is understood that in order to maintain the ideal distribution of enzyme within the working electrode, contact with solvent (water) should not lead to massive detachment of enzyme from the matrix and subsequent migration of enzyme molecules. In other embodiments, enzyme immobilization in the sensing layer 9 can be enhanced by cross-linking. Especially advantageous are enzyme molecules which are cross-linked as a chain, keeping in mind, however, that longer chains result in the enzyme being less effective. In one embodiment, therefore, on average about three to about ten enzyme molecules are linked together, and in other embodiments about 4 to about 8 on average are linked, wherein an average chain length of about five to about seven enzyme molecules is typically useful.

It is possible to add a cross-linking agent, i.e. glutaraldehyd solution, to the paste before drying. However, it is also possible to mix an already cross-linked enzyme into the paste. In one embodiment, an enzyme is used which forms a complex with a hydrophilic partner. After being mixed into a paste which is less hydrophilic or even hydrophobic, as can be achieved by mixing carbon particles with suitable binders, the cross-linked enzyme sits in a local hydrophilic environment which contributes to its stability. One result of a cross-linked enzyme with a hydrophilic partner is that it enhances migration of hydrated analyte molecules towards the enzyme. Thus the wetting of the sensing layer 9 is accelerated which shortens the wet-up time of the sensor after implantation. As a specific example, glucose oxidase cross-linked with dextrane from Roche Diagnostics (Penzberg, Germany, Ident-No. 1485938001) has been found to have such a content of enzyme (approximately 16%) that enough activity (20 to 40 U/mg lyophylisate) can be preserved.

By mixing already cross-linked enzyme with the sensing layer paste containing carbon nanotubes, the trait of the carbon nanotubes to wind up and form clews, which act as macroporous cage structures, is supported by the larger enzyme-dextrane chains, in particular by their aggregation. As a consequence, the cross-linking enzyme will assist in the formation of porous structures of the sensing layer 9.

The sensing layer 9 of the example shown comprises carbon particles with an average size of less than about 1 µm, polymeric binder, enzyme and carbon nanotubes as porous particles 13. The porous particles 13 are more effective to increase the porosity of the sensing layer 9 if they are significantly larger than the carbon particles. In the example shown, the porous particles 13 measure at least about 1 µm, and can be at least about 5 µm, on average. Typically the sensing layer 9 comprises about 50 wt. % to about 70 wt. % polymeric binder, about 20 wt % to about 40 wt. % carbon particles and up to about 20 wt. % (and as low as between about 1 wt. % and about 10 wt. %) porous particles 13 like carbon nanotubes or silica. Carbon nanotubes are an especially advantageous additive as they increase both the porosity and the electrical conductivity of the sensing layer 9. In the embodiment shown schematically in FIG. 1, multiwall carbon nanotubes (research grade, purity>95%) by NanoLab, Newton, Mass., of length about 5 µm to about 20 µm and an average outer diameter of about 25 nm to about 35 nm have been used. The binder is a thermoplastic resin, e.g. on the basis of an epoxy resin or on the basis of polyvinyl chloride (PVC)/polyvinyl alcohol (PVA). Resins on the basis of a fluoro carbon resin, particularly polytetrafluoroethylene, or of polystyrene, may also be used as binders. In the case of PVC/PVA binders, the use of additives like silicone oil can help to adjust the viscosity of the paste.

In this way the sensing layer 9 of the sensor 1 shown in FIG. 1 is adapted and arranged in such a way that in operation after implantation the analyte concentration in the sensing layer 9 is highest at the upper surface, decreases with increasing distance from the upper surface, and is zero at the lower surface which is the furthest point from the analyte-containing body fluid and which touches the contact pad 7. The enzyme loading of the sensing layer 9, i.e. the amount of the enzyme immobilized therein, should be chosen with respect to the porosity and water-permeability of the sensing layer 9.

An important parameter in this respect is the effective diffusion coefficient $D_{eff}$ of the sensing layer 9. The effective diffusion coefficient $D_{eff}$ characterizes the diffusion of the analyte in the sensing layer 9 and depends on the pore volume $\epsilon$ and the tortuosity $\tau$ of the sensing layer 9. Generally, the effective diffusion coefficient $D_{eff}$ can be described as $D_{eff} = D \cdot \epsilon/\tau$, wherein D is the diffusion coefficient of the analyte in water. The quotient $\tau/\epsilon$ is also called hindrance H. In the example shown H is between about 10 and about 1000, and can be between about 50 and about 500.

Another important parameter in this respect is the enzyme loading parameter $\alpha$ which can be described as $\alpha = (V_{max} \cdot d)/(K_M \cdot D)$ wherein $V_{max}$ is the enzyme activity density which determines the maximum speed of analyte conversion, $K_M$ the Michaelis Menten constant of the enzyme, d the thickness of the sensing layer and D the diffusion coefficient of the analyte in water. In one embodiment, the ratio of the effective diffusion coefficient $D_{eff}$ in the sensing layer 9 and the enzyme loading parameter $\alpha$ is in the range of about 10 to about 200.

Figure 2:
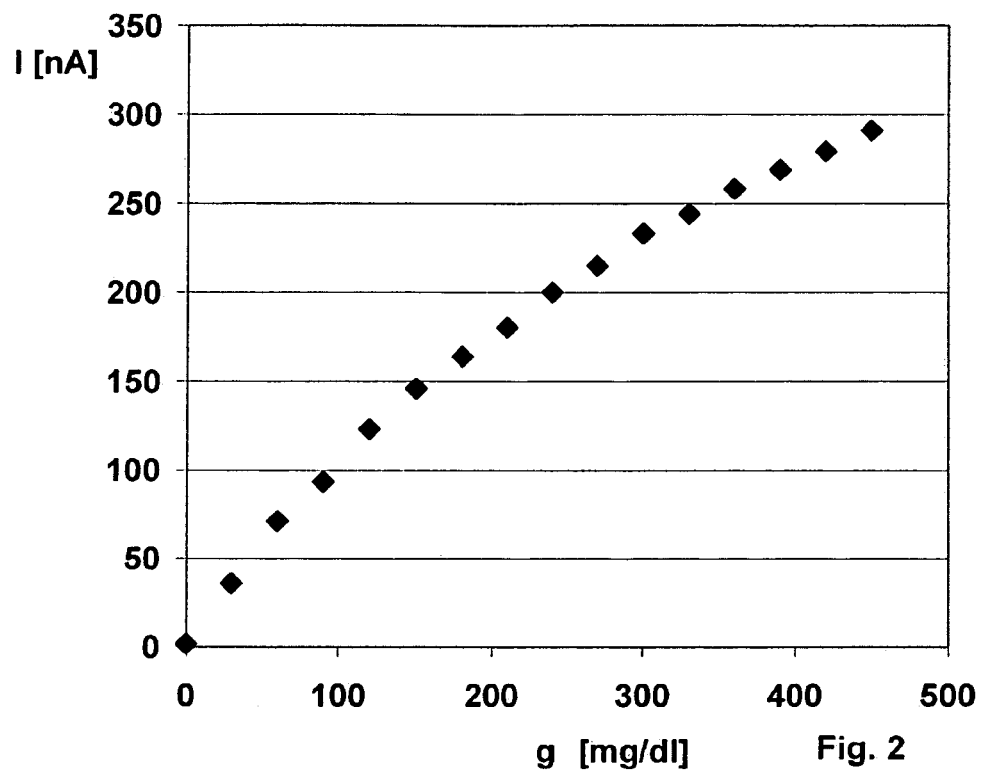
FIG. 2 shows a functional characteristic of the sensor according to FIG. 1 from an in vitro measurement.

FIG. 2 shows the functional characteristic of the sensor described above. The layer 11 has been made from MPC (Lipidure CM 5206, NOF Corp. Japan) by dispensing a 10% solution of MPC in ethanol/water on the electrodes. The measurement current I in nA is plotted versus glucose concentration g in mg/dl. The data shown in FIG. 2 were measured in-vitro in aqueous glucose solution. As can be seen, no saturation at higher glucose concentrations is observed.

Figure 3:
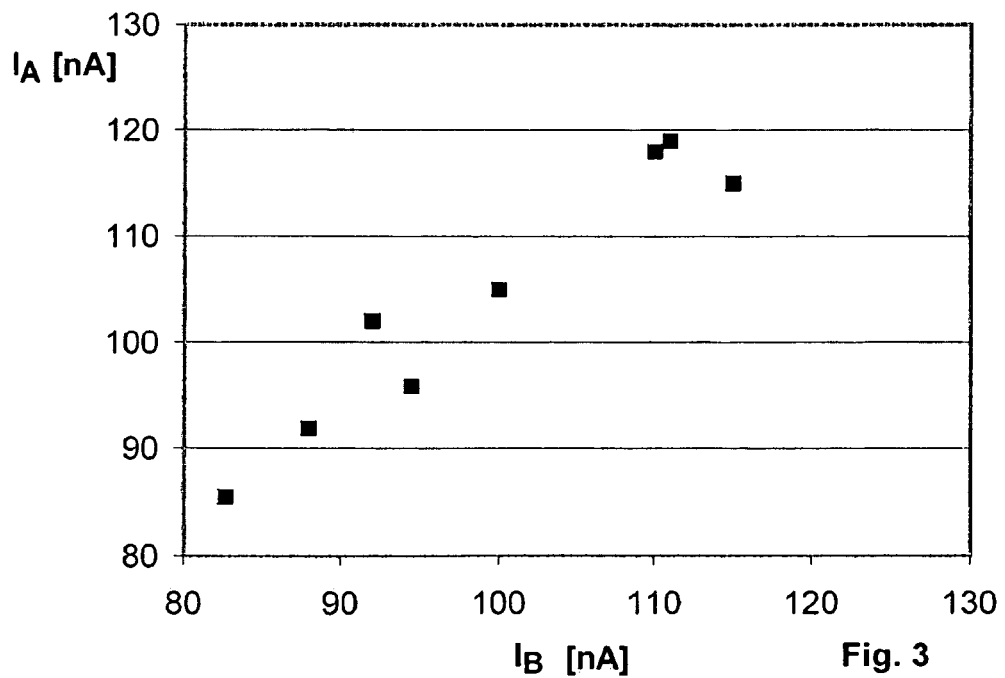
FIG. 3 shows measurement data of the sensor according to FIG. 1 measured in a biomatrix.

FIG. 3 shows for comparison measurement currents $I_A$ and $I_B$ in nA. Currents $I_A$ were measured in-vitro, currents $I_B$ by a sensor in a biomatrix, both at a temperature T=35° C., after the sensors had been equilibrating in the respective medium for 12 hours. Every data point shown belongs thus to a biomatrix measurement and an aqueous glucose solution measurement at identical glucose concentration. The biomatrix used consists of stabilized blood plasma, to which glucose was added in order to obtain the desired glucose concentration. Sensor currents measured in the biomatrix and sensor currents measured in aqueous glucose solution show excellent agreement.

The result is particular noteworthy and demonstrates the profound effects arising from the sensor layout of the embodiment of the present invention. In general, it is expected, that exposure of a sensor 1 to a biomatrix ensures the deposition of proteins, peptides or fibrin on the sensor surface. This process affects the permeability for analytes or water of an outer layer, such as layer 11. In a conventional sensor layout, this layer restricts diffusion of analyte to the sensing layer so that a permeability decrease results in a weaker measurement signal.

However, the signal height of the described sensor 1 is not affected by exposure to a biomatrix, as seen in FIG. 3, since the diffusion of analyte through the layer 11 is not the rate-limiting step in the generation of the signal. Therefore any permeability alteration has very little effect on the signal for the sensor 1 described above.

The present invention is not limited to enzymes using oxygen as co-substrate in the catalytic reaction. The enzyme may be a dehydrogenase as well. For example, a glucose dehydrogenase which does not use oxygen as co-substrate can be distributed within the sensing layer 9. Known dehydrogenases include certain molecules as cofactors for the oxidation of glucose, for example pyrroloquinoline quinone (PQQ), or flavin adenine dinucleotide (FAD) or nicotinamid adenine dinucleotide (NAD), see EP 1 661 516 A1. Any of these dehydrogenases can be used in the sensing layer 9 instead of an oxidase.

Figure 4:
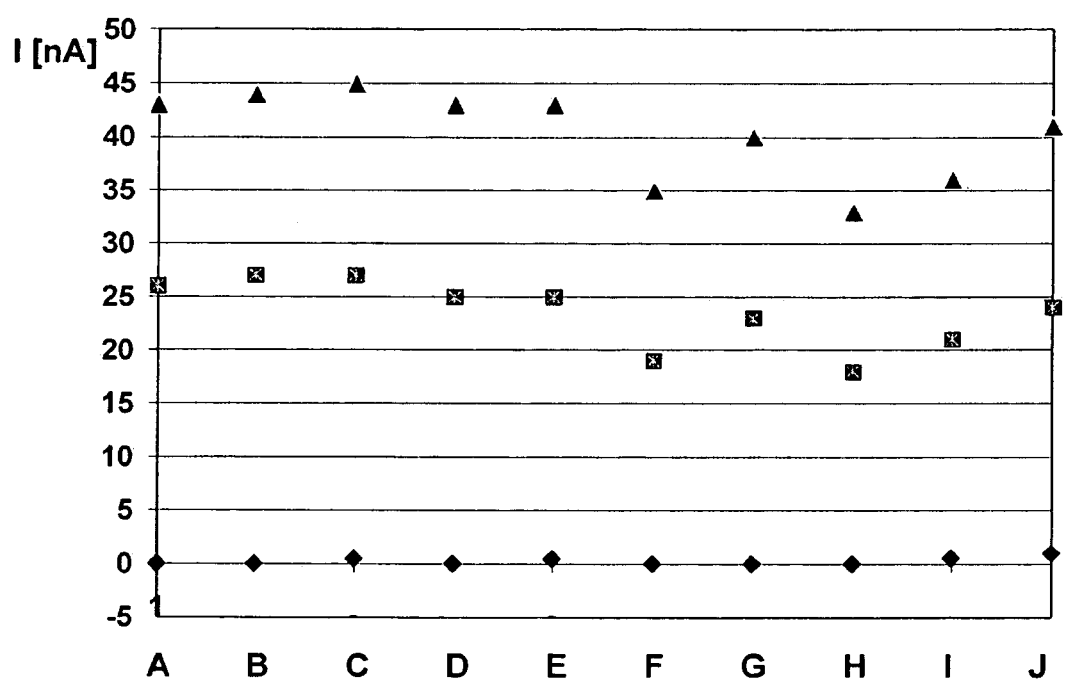
FIG. 4 shows the dependence of sensor current on a diffusion barrier covering the sensing layer of sensors F to J, but not sensors A to E.

FIG. 4 shows the sensor current I in nA, which was measured by sensors A to J in phosphate-buffered aqueous glucose solution of different concentrations. Sensor currents measured at a glucose concentration of 360 mg/dl are depicted by triangles (▲). Sensor currents measured at a glucose concentration of 180 mg/dl are depicted by squares (■). Sensor currents at a glucose concentration of zero are depicted by diamonds (♦).

Sensors A to J differ only with respect to the diffusion barrier applied on top of the sensing layer 9. At sensors A to E a diffusion barrier is lacking, i.e. the sensing layer 9 is in direct contact with the aqueous glucose solution to be measured. Sensors F to J comprise a diffusion barrier covering the sensing layer 9. The diffusion barrier of sensors F to J was provided as a polymer layer made of MPC-like layer 11 in FIG. 1. As can be seen, the sensor currents are only slightly lower for sensors F to J than for sensors A to E. Hence, the diffusion barrier provided by the MPC polymer layer 11 hinders diffusion of analyte molecules only to a very small extent. As the sensor currents of sensors F to J are about 20% lower than sensor currents of sensors A to E, it can be concluded that the diffusion barrier of sensors F to J leads to analyte concentrations on the upper surface of the sensing layer 9 which are only about 20% lower than in the glucose solution surrounding the sensors.

As in the embodiment described previously with reference to FIG. 1 the sensing layers 9 of sensors A to J comprise cross-linked enzymes, i.e. dextranized glucose oxidase which can be purchased by Roche Diagnostics, Penzberg, Germany, Ident-No. 14859389001. The dextranized glucose oxidase has been dissolved in phosphate-buffered solution and mixed into a paste comprising carbon particles, carbon nanotubes and polymeric binder. The sensing layer 9 was dispensed on the contact pad 7 of the working electrode 3 on the sensor substrate 5 with a spot size of about 0.05 mm² to about 0.1 mm², e.g. a circular spot of about 300 µm diameter. The thickness of the sensing layer 9 was about 20 µm. An Ag/AgCl reference electrode 4 of consistent size has also been provided. The counter electrode 2 was of rectangular shape (approximately 400 µm by 900 µm) with an about 20 µm thick layer of carbon paste containing carbon nanotubes.

It is seen in FIG. 4 that the sensor current is barely affected by the presence of the membrane made from MPC.

It can be concluded from this finding that, by the particular choice of the zwitterionic membrane structure, a coating which is highly permeable for solvated glucose has been found. For the construction of a sensor 1, where diffusion-limitation occurs in the sensing layer 9 (see FIG. 1), such a high permeability of the membrane is important. Conversely, the diffusion of analyte through the diffusion barrier provided by the MPC-layer 11, should be hindered as little as possible, ideally the analyte concentration (i.e. signal) at the sensing layer 9 with the coating should be not less than half of the value obtained without the coating.

It should be noted that the optional enzyme-free layer 10 should also have little hindrance to analyte diffusion, therefore its layer thickness should be much thinner than that of the sensing layer 9.

As stated before, mixing of a hydrophilized cross-linked enzyme can yield a very stable function over extended periods of time, since wet-up of the sensing layer is fast and the enzyme distribution stays constant. This is reflected by drift values obtained in measuring the above sensors over 6 days in aqueous glucose solution. For the uncoated sensors, drift ranges from about −0.62% per day to about 0.78% per day, while the coated ones cover a range from about −0.5% to about 1.5% per day. These small drift values have been measured at 37° C.

The particular advantage of measurement stability, i.e. low signal drift, is not limited to a sensor 1 with an enzyme in the sensing layer 9 which uses oxygen as a co-substrate. In fact, the same benefit of cross-linking can be obtained by using a cross-linked dehydrogenase which does not need oxygen as a co-substrate in the catalytic reaction. For example, a dextranized glucose dehydrogenase or a pegylated dehydrogenase (PEG: polyethylene glycol) can be brought into the sensing layer 9.

Figure 5:
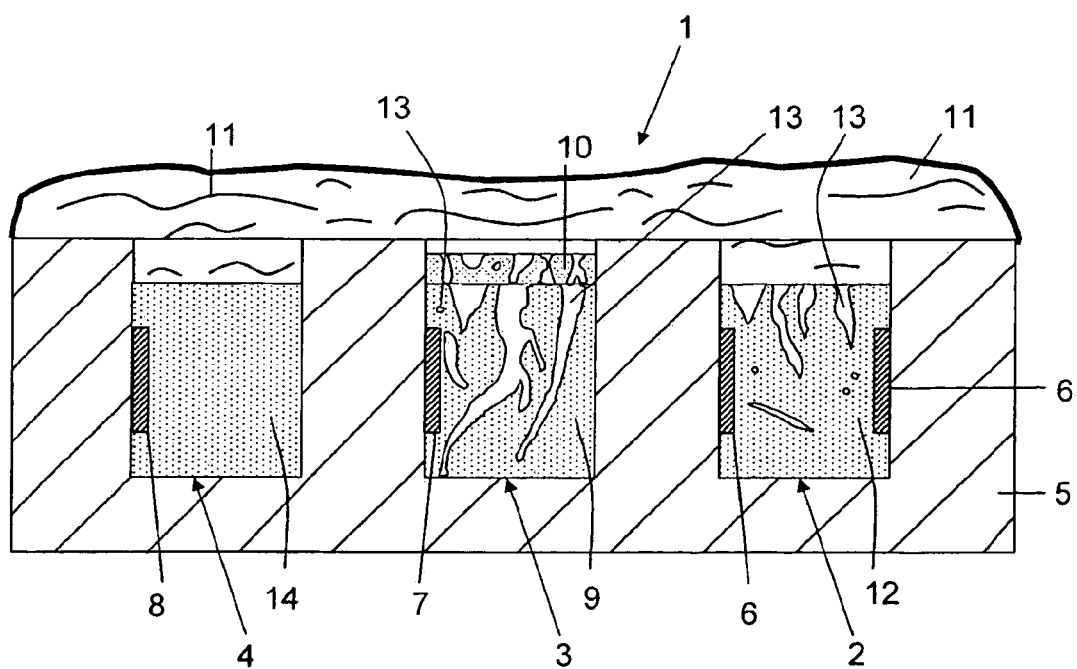
FIG. 5 shows a second exemplary embodiment of a sensor according to the present invention in a cross section view.

In the sensor 1 shown in FIG. 1 the sensing layer 9 is arranged on the contact pad 7. Further, the sensing layer 9 has a lower surface facing the contact pad 7 and an upper surface facing away from the contact pad 7, or more generally the sensing layer 9 has having a lower surface facing the support member 5 and an upper surface facing away from the support member 5 toward the analyte-containing body fluid. Correspondingly the layers 12, 14 are arranged the contact pads 6, 8. FIG. 5 shows an amended embodiment of the sensor 1 of FIG. 1. The embodiment of FIG. 5 corresponds to the embodiment of FIG. 1, with the difference that the electrodes with the contact pads 6, 7, 8 being placed on the side of the water-permeable layers 9, 12 and 14, in contrast to FIG. 1. It is also possible to place a contact pad 6, 7, 8 on two sides of the respective layer 9, 12, 14, as illustrated for the contact pad 6 of the water-permeable layer 12 of counter electrode 2. This contact pad 6 can also be formed so that it encloses the layer 12 from all sides. In all cases where the contact pad 6, 7, 8 sits on the side of the permeable layer 9, 12, 14, the surface of the layer 9, 12, 14 facing away from the analyte-containing body fluid is directly in contact with the support member 5.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even, important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. An amperometric sensor configured for implantation into the living body of a human or animal to measure the concentration of an analyte in a body fluid, said sensor comprising a counter electrode and a working electrode, said working electrode comprising a sensing layer having a thickness of between at least about 5 µm and 100 µm and which is generally permeable for water and arranged on a support member adjacent to a contact pad, said sensing layer comprising an immobilized enzyme capable of acting catalytically in the presence of the analyte to cause an electrical signal, the sensing layer having an upper surface facing the body fluid and facing away from the support member and a lower surface facing away from the body fluid and facing towards the support member, wherein the immobilized enzyme is distributed in the sensing layer in such a way that the enzyme concentration in the middle between the upper and lower surfaces is at least as high as on the upper surface of the sensing layer, further wherein the sensing layer has an effective diffusion coefficient $D_{\it eff}$, which characterizes the diffusion of the analyte in the sensing layer and is about 10-times to about 1000-times lower than the diffusion coefficient D of the analyte in water, the sensor further comprising a diffusion barrier permeable to the analyte covering the sensing layer, the diffusion barrier having a layer with a thickness of between 1 µm and 3 µm.

2. The sensor according to claim 1, wherein the enzyme comprises a cross-linked enzyme.

3. The sensor according to claim 2, wherein the cross-linked enzyme forms a complex with a hydrophilic partner.

4. The sensor according to claim 2, wherein the cross-linked enzyme has an average chain length of about three to about ten enzyme molecules.

5. The sensor according to claim 4, wherein the average chain length is about 4 to about 8 enzyme molecules.

6. The sensor according to claim 1, wherein the sensing layer is covered by the diffusion barrier which hinders diffusion of analyte molecules to such an extent that after implantation into the living body of a human or an animal the analyte concentration at the upper surface of the sensing layer is at most about ten times lower than in the body fluid surrounding the implanted sensor and wherein the diffusion barrier comprises an electrically conductive enzyme-free layer comprising carbon particles and a polymeric binder.

7. The sensor according to claim 6, wherein after implantation into the living body of a human or an animal the analyte concentration at the upper surface of the sensing layer is at most about five times lower than in the body fluid surrounding the implanted sensor.

8. The sensor according to claim 1, wherein the sensing layer contains porous particles.

9. The sensor according to claim 8, wherein the porous particles comprise one or both of silica and carbon nanotubes.

10. The sensor according to claim 8, wherein the porous particles increase both the porosity and the electrical conductivity of the sensing layer.

11. The sensor according to claim 8, wherein the porous particles measure on average between at least about 1 µm and about 5 µm.

12. The sensor according to claim 1, wherein the sensing layer is adapted and arranged in such a way that in operation after implantation the analyte concentration in the sensing layer is highest at the upper surface, decreases with increasing distance from the upper surface, and is zero at the lower surface which is the furthest point from the analyte-containing body fluid.

13. The sensor according to claim 1, wherein the contact pad of the working electrode is an electrically conductive film.

14. The sensor according to claim 13, wherein the electrically conductive film comprises a metallic film or a polymer film.

15. The sensor according to claim 1, wherein the working electrode is arranged on a support member made of a plastic material.

16. The sensor according to claim 1, wherein the sensing layer has a thickness of between at least about 20 µm and about 70 µm.

17. The sensor according to claim 1, wherein the sensing layer comprises carbon particles and a polymeric binder.

18. The sensor according to claim 1, wherein the sensing layer is covered by the diffusion barrier which hinders diffusion of analyte molecules to such an extent that after implantation into the living body of a human or an animal the analyte concentration at the upper surface of the sensing layer is at most about ten times lower than in the body fluid surrounding the implanted sensor.

19. The sensor according to claim 18, wherein the sensing layer is covered by the diffusion barrier which hinders diffusion of analyte molecules to such an extent that after implantation into the living body of a human or an animal the analyte concentration at the upper surface of the sensing layer is at most about five times lower than in the body fluid surrounding the implanted sensor.

20. The sensor according to claim 18, wherein the diffusion barrier comprises a dialysis layer.

21. The sensor according to claim 18, wherein the diffusion barrier comprises a polymer layer made of a polymer having a zwitterionic structure.

22. The sensor according to claim 1, wherein the sensing layer includes lateral surfaces which are generally impervious for the body fluid.

23. The sensor according to claim 1, wherein the sensing layer is electrically conductive.

24. The sensor according to claim 23, wherein the sensing layer has an electrical conductivity of at least about $1\,\Omega^{-1}cm^{-1}$.

25. The sensor according to claim 1, wherein the enzyme comprises an oxidase.

26. The sensor according to claim 1, wherein the enzyme comprises a dehydrogenase.

27. The sensor according to claim 1, wherein the enzyme is distributed generally equally throughout the sensing layer.

28. The sensor according to claim 1, wherein said sensing layer is arranged on the contact pad and the sensing layer has a lower surface facing the contact pad and an upper surface facing away from the contact pad.

29. A method for manufacturing the amperometric sensor according to claim 1, said method comprising the following steps: mixing carbon particles, enzyme and a polymeric binder to create a paste; applying said paste adjacent to a contact pad on a support member of said sensor, hardening that paste into a porous sensing layer.

* * * * *